(12) United States Patent
Iyer et al.

(10) Patent No.: US 7,816,928 B2
(45) Date of Patent: *Oct. 19, 2010

(54) DETERMINATION OF EQUIVALENT SERIES RESISTANCE

(75) Inventors: Rajesh V. Iyer, Eden Prairie, MN (US); Ryan J. Jensen, White Bear Township, MN (US); Curtis E. Burgardt, Sauk Rapids, MN (US); Susan A. Tettemer, Fridley, MN (US); Daniel J. Koch, Lakeville, MN (US); Simon E. Goldman, St. Louis Park, MN (US)

(73) Assignee: Medtronic, Inc., Minneapolis, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/396,215

(22) Filed: Mar. 2, 2009

(65) Prior Publication Data

US 2009/0160465 A1 Jun. 25, 2009

Related U.S. Application Data

(63) Continuation of application No. 11/236,369, filed on Sep. 27, 2005, now Pat. No. 7,538,563.

(51) Int. Cl.
*G01R 27/08* (2006.01)
*G01R 27/00* (2006.01)
(52) U.S. Cl. .................... 324/691; 324/707; 702/65
(58) Field of Classification Search ................. 324/691
See application file for complete search history.

(56) References Cited

U.S. PATENT DOCUMENTS

| | | | |
|---|---|---|---|
| 6,765,780 B2 * | 7/2004 | Brendel et al. | 361/302 |
| 6,941,233 B2 * | 9/2005 | Ennis et al. | 702/57 |
| 7,499,817 B2 * | 3/2009 | Iyer et al. | 702/65 |
| 7,538,563 B2 * | 5/2009 | Iyer et al. | 324/691 |
| 2003/0127913 A1 * | 7/2003 | Roberts et al. | 307/89 |
| 2004/0019367 A1 * | 1/2004 | Dahl et al. | 607/37 |

* cited by examiner

*Primary Examiner*—Jeff Natalini
(74) *Attorney, Agent, or Firm*—Carol F. Barry

(57) ABSTRACT

A determination of an equivalent series resistance (ESR) effect for high frequency filtering performance of a filtered feed-through assembly is described. A low frequency signal is introduced to a filtered feed-through assembly. ESR limit of the filtered feed-through is determined based on the low frequency signal.

16 Claims, 7 Drawing Sheets

DETERMINATION OF EQUIVALENT SERIES RESISTANCE

RELATED APPLICATION

This application is a continuation of U.S. patent application Ser. No. 11/236,369, filed Sep. 27, 2005 entitled "Determination of Equivalent Series Resistance". This application is also related to U.S. patent application Ser. No. 11/235,944 filed on Sep. 27, 2005 and entitled "DETERMINATION OF EQUIVALENT SERIES RESISTANCE".

FIELD OF THE INVENTION

The present invention relates to measurement techniques and, more specifically, to determination of equivalent series resistance (ESR) effect on high frequency filtering performance of a filtered feed-through assembly.

BACKGROUND OF THE INVENTION

Implantable medical devices (IMDs) detect and correct a variety of medical conditions in patients. Exemplary IMDs include implantable pulse generators (IPGs) or implantable cardioverter-defibrillators (ICDs) that deliver electrical stimulation to tissue of a patient. IMDs typically include, inter alia, a control module, a capacitor, and a battery. These components are housed in a container that is hermetically sealed to prevent liquid from contacting the electronic components therein. To connect with the electronic components, a feed-through assembly is coupled to the container. The feed-through assembly forms an aperture in the container, which allows an electrical lead to pass therethrough.

Electromagnetic interference (EMI) may affect the operation of an IMD. EMI is any electromagnetic disturbance, phenomenon, signal, or emission that causes or can cause an undesired response in an IMD. To address EMI, an EMI filter is incorporated into a feed-through assembly. A typical filtered feed-through assembly consists of a conductive line, a ferrule, an insulator member (e.g. glass, ceramic etc.), at least one capacitor, and a seal. The filtered feed-through assembly is configured such that the seal lines an aperture located in the ferrule. The insulator member is placed in the aperture adjacent to the seal. The conductive line is connected to the ferrule and the capacitor. A lead (e.g. wire) or a terminal pin to the sealed container is inserted through another aperture in the insulator member, which provides an electrical connection to the components within the IMD.

The filtered feed-through assembly capacitor acts as a low pass filter to prevent EMI from affecting the operation of the IMD. A low pass filter allows low frequency signals to pass but prevents high frequency signals from passing therethrough. The performance of the EMI filter is determined by insertion loss. Insertion loss results from the insertion of a device in a transmission line, expressed as the reciprocal of the ratio of the signal power delivered to that part of the line following the device to the signal power delivered to that same part before insertion. Insertion loss depends upon the number of components in the EMI filter, impedance value of each EMI filter component, the frequency at which the insertion loss is measured, equivalent series resistance (ESR), and equivalent series induction (ESL).

Insertion loss measurement at high frequencies is difficult due to increased noise detected for high frequency signals. To determine insertion loss at a high frequency, a radio frequency (RF) shield is welded to the filtered feed-through assembly. The RF shield isolates the input and output ends of the filtered feed-through assembly during the test. The welding operation and the RF shield itself increase the cost of producing an IMD. Additionally, this insertion loss measurement method cannot be used on a large-scale basis.

Alternatively, insertion loss may be measured without a RF shield welded to the filtered feed-through assembly. However, this type of insertion loss measurement is unreliable. It is therefore desirable to overcome the limitations associated with conventional testing systems.

DETAILED DESCRIPTION

Figure 1:
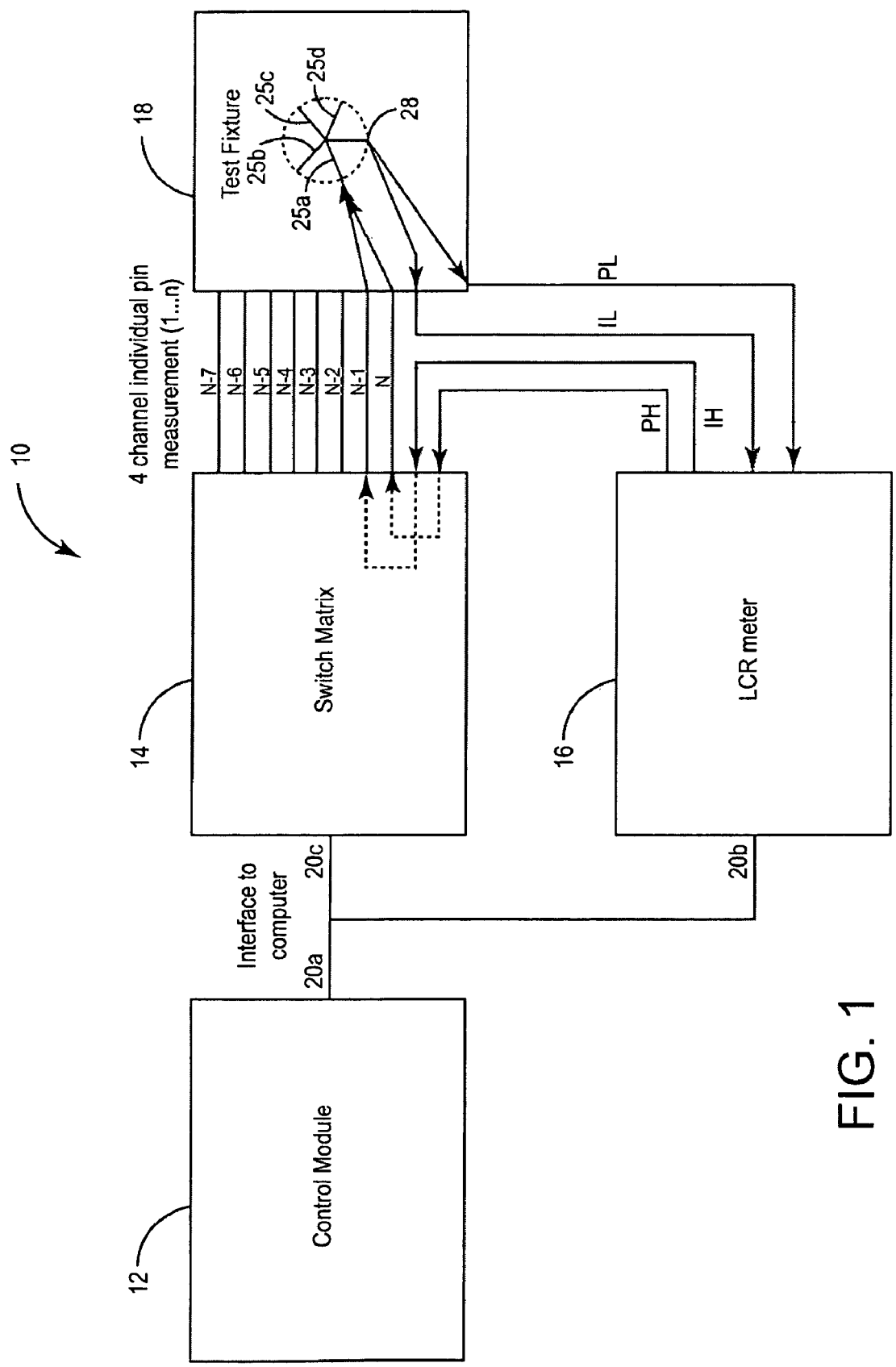
FIG. 1 depicts a block diagram of an exemplary testing system.

The following description of an embodiment is merely exemplary in nature and is in no way intended to limit the invention, its application, or uses. For purposes of clarity, the same reference numbers are used in the drawings to identify similar elements. As used herein, the term "module" refers to an application specific integrated circuit (ASIC), an electronic circuit, a processor (shared, dedicated, or group) and memory that execute one or more software or firmware programs, a combinational logic circuit, or other suitable components that provide the described functionality.

Generally, the present invention is directed to measurement of insertion loss related to a device (e.g., filtered feed-through assembly) over a certain frequency range. For example, the frequency range of about 450 megahertz (MHz) to about 3 gigahertz (GHz) is used to determine the effectiveness of the low pass filter (e.g., capacitor(s) in the filtered feed-through assembly) disposed in an implantable medical device (IMD). This insertion loss measurement technique may be used over any other appropriate frequency range for a particular device.

Specifically, the present invention relates to measurement of equivalent series resistance (ESR) effect on high frequency filtering performance of a filtered feed-through assembly for a device. A set of insertion loss data at a first high frequency (e.g. 450 MHz to about 3 GHz) is determined for a filtered feed-through assembly. A set of insertion loss data is generated at a second high frequency (e.g. 2450 MHz) for the filtered feed-through assembly. A set of ESR data is generated at a low frequency (e.g. 2 MHz) for the filtered feed-through assembly. The set of ESR data at the low frequency is correlated to the insertion loss generated at a first high frequency. This correlation may be graphically represented or tabulated. A prediction interval that includes upper and lower limits is superimposed on the graph. A specified insertion loss data (e.g. 30 dB) is selected for a particular device. An ESR limit for a low frequency signal is determined based upon the specified insertion loss data and the upper limit of the prediction interval. The ESR limit is compared to ESR values of manufactured filtered feed-through assemblies. Filtered feed-through assemblies are of acceptable quality when their ESR value is below the ESR limit. In contrast, filtered feed-through assemblies are rejected that exhibit an ESR value above the ESR limit.

The present invention increases the accuracy of determining the ESR effect at high frequency signals filtered via a filtered feed-through assembly. Additionally, the present invention reduces the cost of producing an implantable medical device by eliminating welding of a shield to a feed-through assembly. Furthermore, the present invention may be implemented on a mass production scale.

FIG. 1 depicts a test system 10 that determines ESR effect on high frequency filtering performance of a device under test (DUT). Test system 10 includes a control module 12, a switch matrix 14, an inductance, capacitance, resistance (LCR) meter or impedance meter 16 (i.e. measurement meter), and a test fixture 18.

Control module 12 is typically a computer that includes a parallel port (not shown) connected to bus 20a. The parallel port generally includes 32 lines and 16 input/output ports. Since two lines are associated with a single input/output port, multiple busses may be connected to the parallel port. Control module 12 connects to LCR meter 16 and switch matrix 14 via buses 20a, 20b, and 20c respectively. Control module 12 inputs a control signal over buses 20a, 20b to LCR meter 16. LCR meter 16 is configured to measure and transmit to control module 12 the inductance, capacitance, and resistance associated with a DUT that is connected to test fixture 18.

Figure 2:
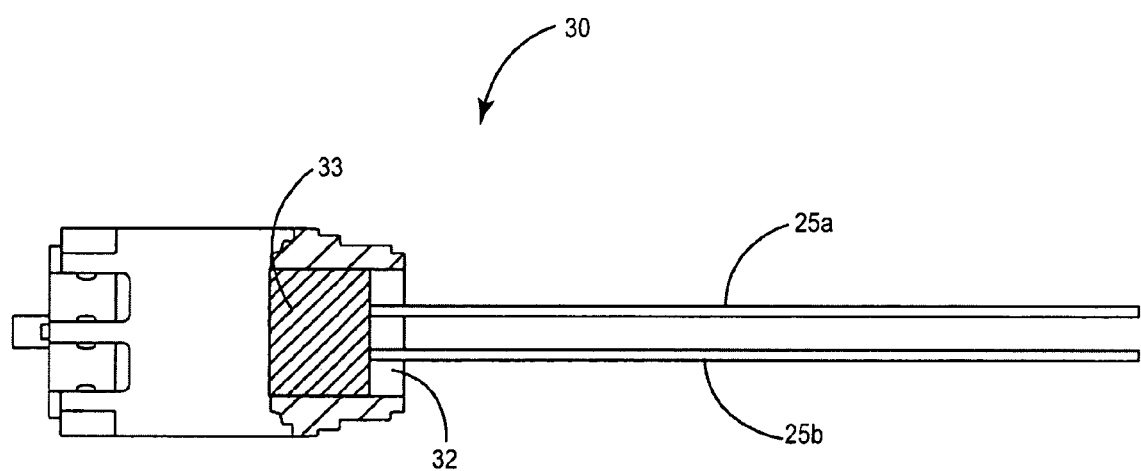
FIG. 2 is a perspective side view of an exemplary feed-through assembly.
Figure 3:
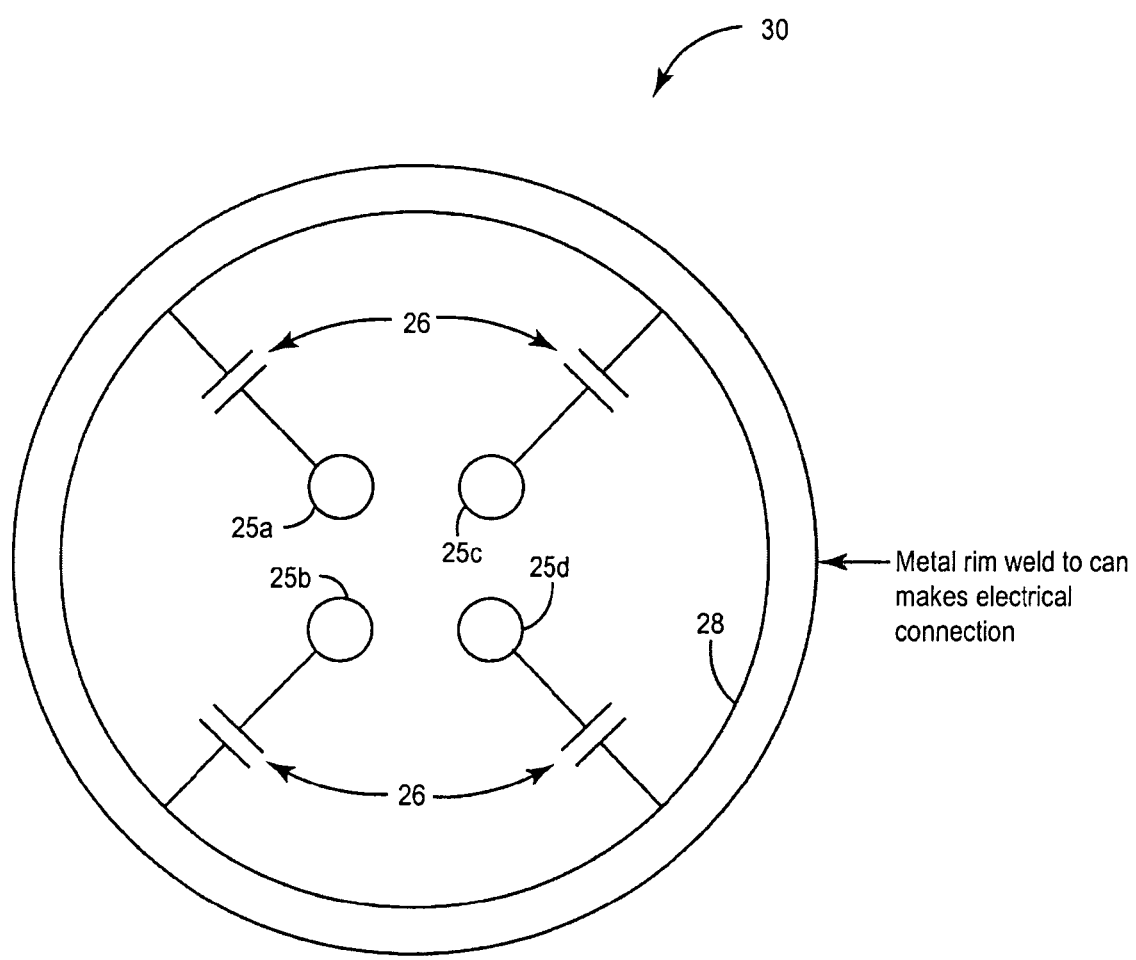
FIG. 3 is a cross-sectional view of an exemplary filtered feed-through assembly.
Figure 4:
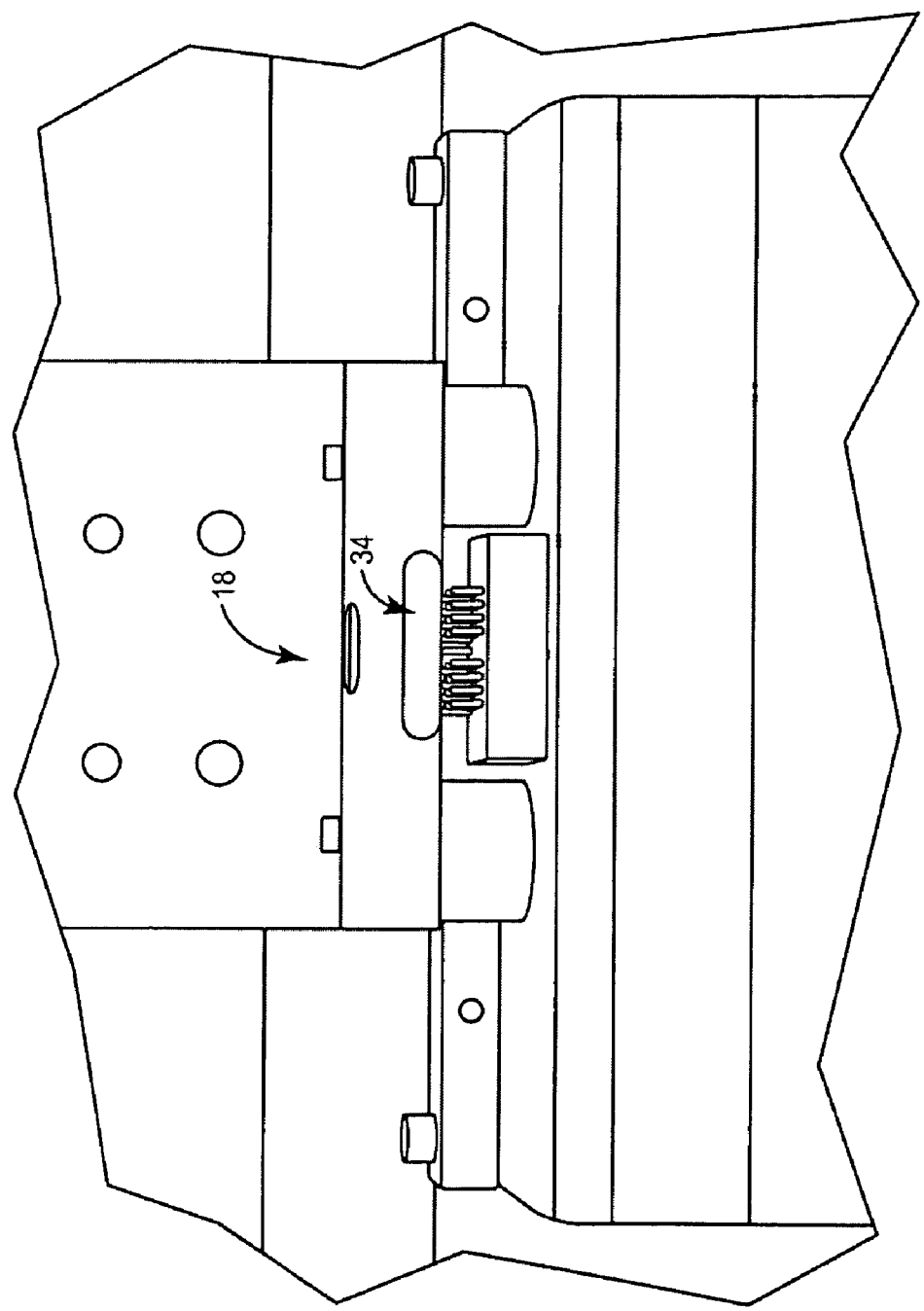
FIG. 4 is a perspective side view of an exemplary test fixture and a device under test.
Figure 5:
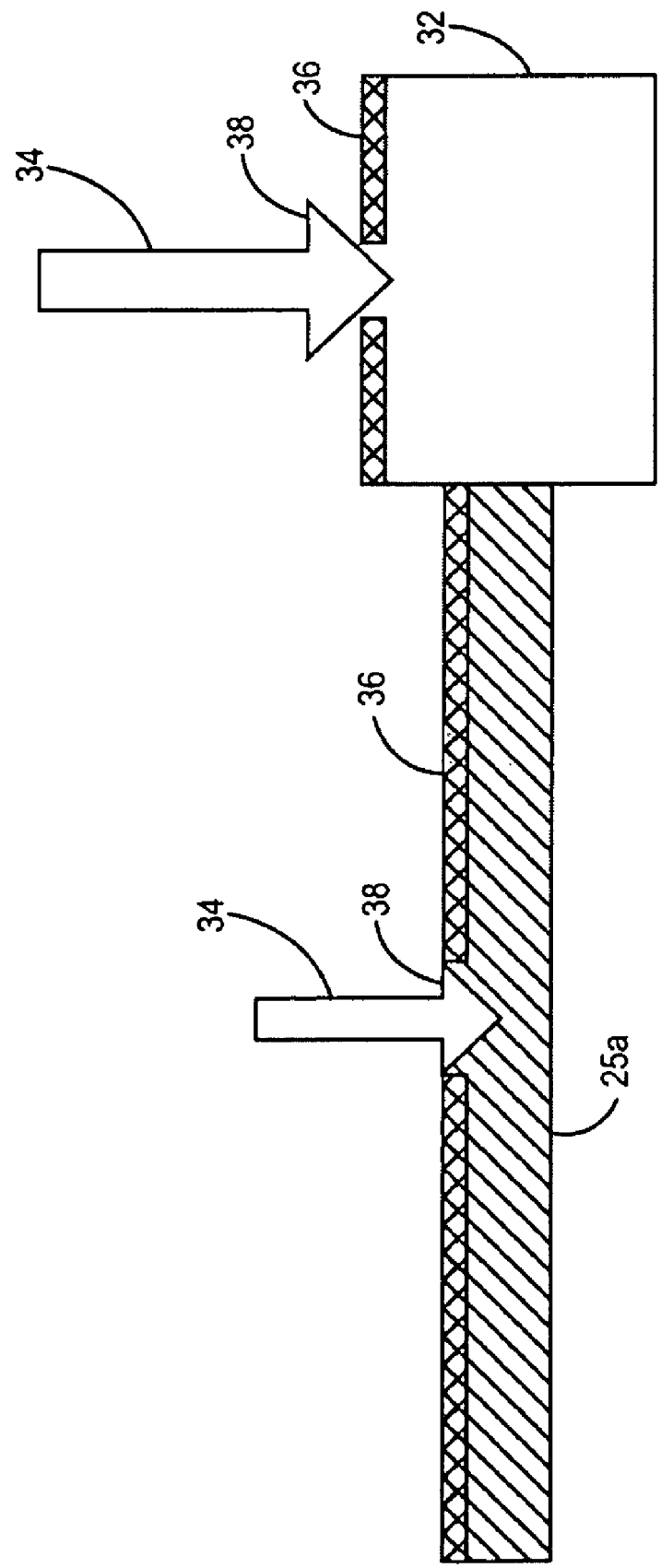
FIG. 5 is a portion of an exemplary test fixture with a pin piercing an oxide layer to connect with a ferrule of a filtered feed-through assembly.

In one embodiment, the DUT is a filtered feed-through assembly 30 depicted in FIGS. 2-3. Filtered feed-through assembly 30 consists of one or more conductive lines 25a-b that include nonpolarized capacitors 26, a ferrule 32, and an insulator member (e.g. glass, ceramic etc.) 33. FIGS. 4-5 depict test fixture's 18 set of pogo pins 34 include spear points 38 that are configured to pierce an oxide layer 36. At least one pogo pin 34 directly contacts ferrule 32 to securely form a ground connection. The secure ground connection assists in detecting and measuring more accurate data than conventional systems. In addition to providing accurate insertion loss and ESR data, test system 10 also provides more accurate data related to measurement of capacitance, displacement factors, high voltage resistance, and other suitable factors.

Figure 6:
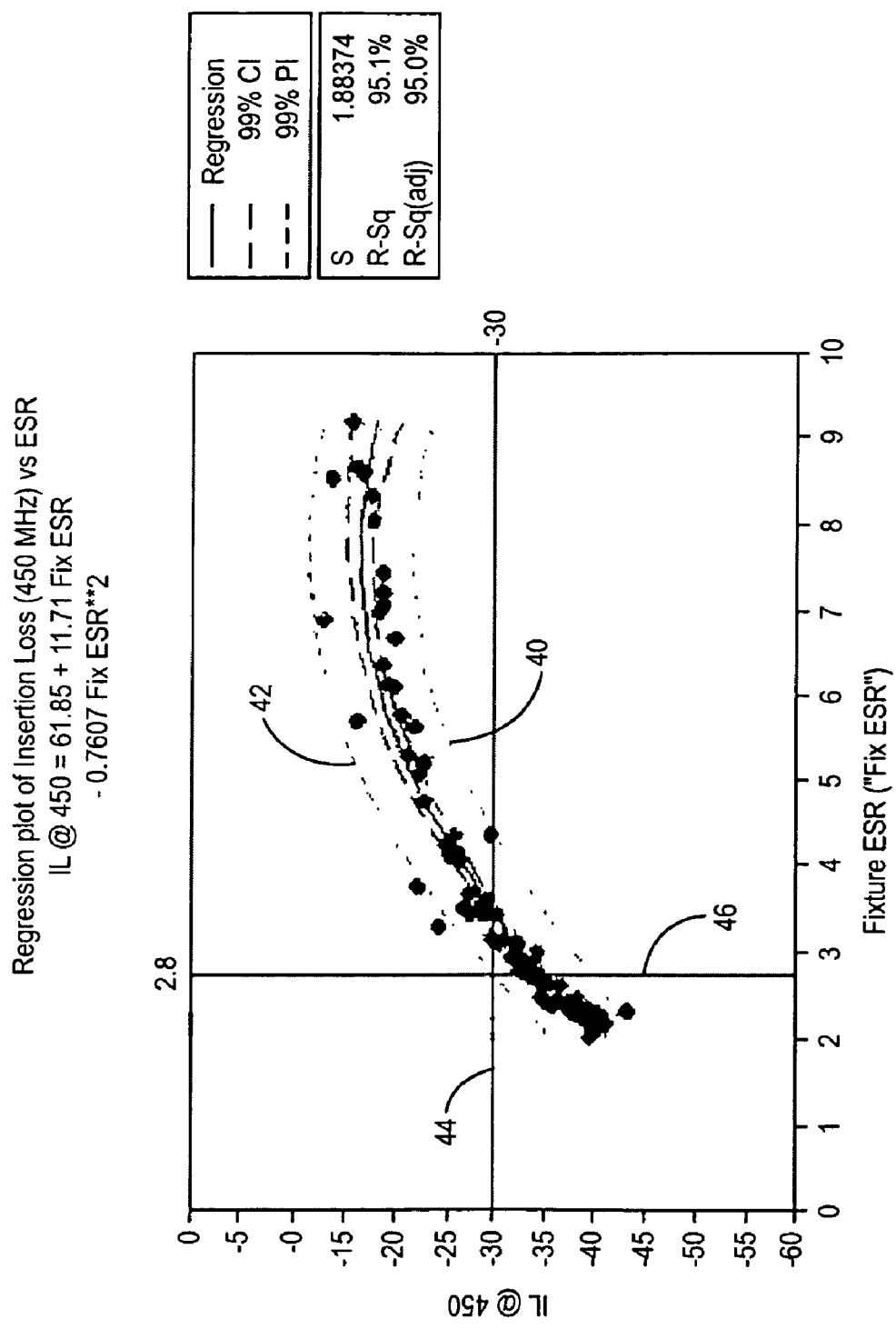
FIG. 6 is a graph illustrating insertion loss versus equivalent series resistance for a device evaluated by the testing system of FIG. 1.
Figure 7:
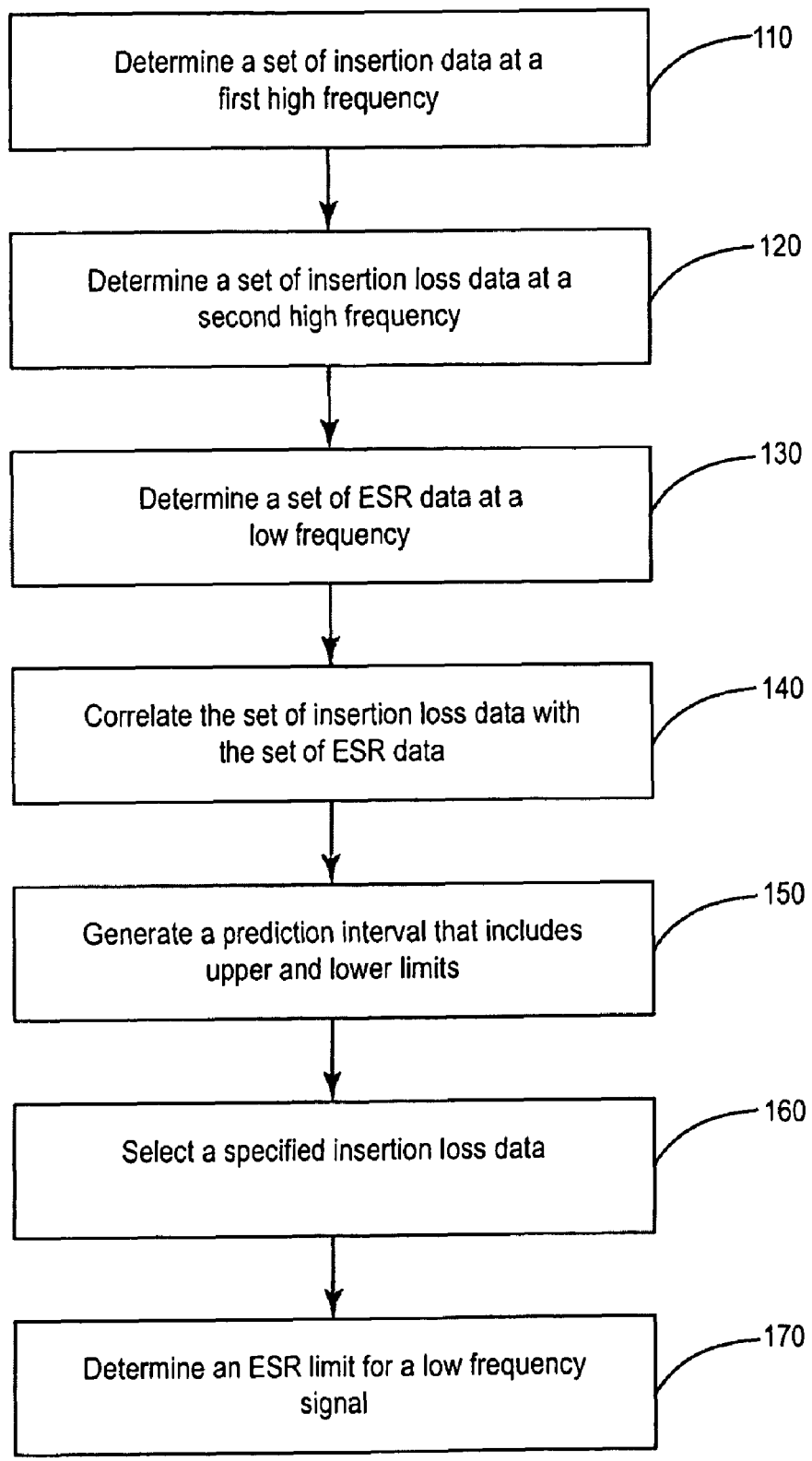
FIG. 7 is a flow diagram of a method to predict or estimate insertion loss associated with a feed-through assembly.

LCR meter 16 inputs a test signal at a certain frequency to switch matrix 14 over conductive lines PH, IH. PH is a positive voltage conductive line whereas IH is a positive current conductive line. Based upon the signal from LCR meter 16, switch matrix 14 selects one of four channels to test one or more conductive lines 25a-d of a feed-through assembly 30. A first channel is formed by conductive lines N-7 and N-6; a second channel is formed by conductive lines N-5 and N-4; a third channel is formed by conductive lines N-3 and N-2; and a fourth channel is formed by conductive lines N-1 and N. Switch matrix 14 then signals a conductive line 25a over the selected channel. A signal is then transmitted from conductive line 25a to LCR meter 16 over negative voltage conductive line PL and negative current conductive line IL. LCR meter 16 determines the ESR for test fixture 18 and the insertion loss at two different high frequencies (e.g. 450 megahertz (MHz) and at 2450 MHz etc.). Generally, a high frequency ranges from about 9 KHz to about 10,000 MHz. The ESR is also measured at 2 MHz for the filtered feed-through assembly. The data is transmitted to control module 12. This process is repeated for a set of filtered feed-through assemblies. Control module 12 then executes regression analysis instructions that correlate insertion loss data obtained at a high frequency to ESR data obtained at a low frequency, as depicted in the graph of FIG. 6. Exemplary regression analysis software is commercially available from Minitab located in State College, Pa. Regression analysis is described in detail by W. Mendenhall and T. Sincich, Statistics For Engineering And the Sciences (4th Ed. 1995), which is incorporated by reference, in relevant parts.

An example of simple regression analysis is presented below. Regression analysis determines the prediction interval (PI) for insertion loss, as depicted in FIG. 6. PI, defined by lower and upper limits 40, 42, is an interval that quantifies the degree of uncertainty in a future prediction relative to insertion loss of a DUT. The formula to calculate the PI for insertion loss, defined as y, is as follows:

$$\hat{y} \pm t\left(n-2, \frac{\alpha}{2}\right) \cdot s_e \cdot \sqrt{1 + \frac{1}{n} + \frac{(x_0 - \bar{x})^2}{SSx}}$$

where, t is the Student's t-distribution statistic obtained from tabulated data, t (df,α) is the critical value for the Student's t-distribution, df=(n−2) is the degree of freedom, =probability of type 1 error=0.01, n=sample size (i.e. number of pieces of data in one sample)

$\bar{x}$=is the average value for x, $X_0$=ESR measured at a low frequency, $$s_e^2 = \frac{\left(\sum y^2\right) - (b_0)\left(\sum y\right) - (b_1)\left(\sum xy\right)}{n-2}$$

$$b_1 = \frac{\sum (x - \bar{x})(y - \bar{y})}{\sum (x - \bar{x})^2}$$

$\bar{y}$=the average value of insertion loss data $$b_0 = \frac{\sum y - (b_1 \cdot \sum x)}{n}$$

$\hat{y}$=predicted value of y for a given x $$SSx = \sum x^2 - \frac{\left(\sum x\right)^2}{n}$$

The lower and upper PI limits 40, 42 are determined from the confidence level and the standard error of the prediction. The PI is generally wider than a confidence interval because of the added uncertainty involved in predicting a single response versus the mean response. The PI is a discrete determination that is performed at a chosen Xo over a desired ESR range to create a curve. In the present example, Xo is selected over an ESR range such that the upper limit 40 for insertion loss crosses the desired insertion loss specification limit 44 (Y-axis). In this example, the desired insertion loss limit is −30 decibels (dB). From this data, the ESR limit 46 is determined to be 2.8Ω since this is the point at which upper limit 42 crosses the desired insertion loss limit 44.

Using the above formula, the value of the Y interval (i.e., insertion loss) is predicted in an iterative manner for a given $X_0$ (ESR). Table 1 summarizes ESR data at a lower frequency (e.g. 2 MHz) and the upper and lower limits for insertion loss.

TABLE 1

Tabulated data for a filtered feed-through assembly

| $X_0$ (ESR at 2 MHz) Ω | Prediction Limit For Insertion Loss at 450 MHz (Lower Limit) | Prediction Limit For Insertion Loss at 450 MHz (Upper Limit) |
|---|---|---|
| 2.3 | −43.9578 | −33.9257 |
| 2.4 | −43.1368 | −33.1196 |
| 2.5 | −42.3326 | −32.3272 |
| 2.6 | −41.5451 | −31.5485 |
| 2.7 | −40.7741 | −30.7837 |
| 2.75 | −40.3948 | −30.4065 |
| 2.8 | −40.0196 | −30.0329 |
| 2.85 | −39.6484 | −29.6628 |
| 2.9 | −39.2813 | −29.2963 |
| 2.95 | −38.9182 | −28.9333 |
| 3 | −38.5592 | −28.5739 |

The ESR limit is based on a minimum insertion loss requirement. ESR limit 46 is used to accept or reject a part. In particular, ESR limit 46 is compared to the ESR exhibited by the DUT. If the ESR of the DUT is below ESR limit 46, the DUT satisfies quality specifications. However, if the DUT's ESR value exceeds ESR limit 46, the DUT does not meet quality specifications. DUT's are rejected that exceed ESR limit 46. In addition to using the ESR limit 46 to determine the quality of a DUT, the ESR value measured on the DUT can also be used to predict the insertion loss of the DUT using the same method.

FIG. 6 is a flow diagram of one method to determine an ESR limit at a low frequency. At operation 110, a set of insertion loss data at a first high frequency (e.g. 450 MHz) is determined for a filtered feed-through assembly. At operation 120, a set of insertion loss data is generated at a second high frequency (e.g. 2450 MHz) for the filtered feed-through assembly. At operation 130, a set of ESR data is generated at a low frequency (e.g. 2 MHz) for the filtered feed-through assembly. The set of ESR data at a low frequency is correlated to the insertion loss generated at a first high frequency. This correlation may be graphically represented or tabulated. At operation 140, the set of insertion loss data is correlated to the set of ESR data. At operation 150, a prediction interval that includes upper and lower limits is generated and superimposed on the graph. At operation 160, a specified insertion loss value (e.g. 30 dB) is selected. The specified insert in loss value is based upon the desired minimal quality that is sought for a manufactured device (e.g. filtered feed-through assembly). At operation 170, an ESR limit for a low frequency signal is determined. The ESR limit is based upon the first insertion loss data and the upper limit of the prediction interval. The ESR limit is then used to reject or accept manufactured feed-through assemblies.

The present invention has numerous applications. For example, while the figures relate to quadripolar filtered feed-through assemblies, other types of feed-through assemblies may also rely on this process to reliably produce quality feed-through assemblies. Additionally, the operation described herein may be implemented entirely automatically or manually. Moreover, skilled artisans appreciate that measurement techniques are not polarity sensitive. Accordingly, techniques of the invention may be implemented with PH having a negative voltage and PL having a positive voltage. Similarly, IH can possess a negative current and IL can be a positive current. Furthermore, while the present invention describes rejection of a manufactured device (e.g. filtered feed-through assembly etc.) that exceeds an ESR limit, skilled artisans understand that principles of the invention may also be configured in a manner such that a manufactured device is rejected that is below an ESR limit.

The description of the invention is merely exemplary in nature and, thus, variations that do not depart from the gist of the invention are intended to be within the scope of the invention. Such variations are not to be regarded as a departure from the spirit and scope of the invention.

The invention claimed is:

1. A test system to determine if a filtered feed-through assembly is of acceptable quality, wherein the filtered feed-through assembly includes one or more conductive lines and a ferrule, the test system comprising:

a test fixture comprising a plurality of pins electrically connectable to a filtered feed-through assembly, wherein each pin includes a sharp distal tip, and further wherein the plurality of pins comprises at least a conductor probe pin and at least a ground probe pin, the conductor probe pin being electrically connectable to one of the one or more conductive lines and the ground probe pin being electrically connectable to the ferrule to provide a ground connection;

a measurement meter electrically connectable via the conductor probe pin of the test fixture to a filtered feed-through assembly under test and electrically connectable via the ground probe pin of the test fixture to the filtered feed-through assembly under test, wherein the measurement meter is controllable to transmit signals at one or more frequencies to be applied to the filtered feed-through assembly under test and to measure one or more electrical parameters of the filtered feed-through assembly under test for use in determining at least equivalent series resistance (ESR) data and insertion loss data for the filtered feed-through assembly under test; and a control module coupled to the measurement meter to control measurement of the one or more electrical parameters of the filtered feed-through assembly under test, and further wherein the control module comprises a processor operable to execute instructions to correlate ESR data to insertion loss data for one or more filtered feed-through assemblies and to determine an ESR limit based on the correlation and a selected desired insertion loss limit, wherein the ESR limit is used to determine if a filtered feed-through assembly is of acceptable quality, wherein the sharp distal tip of at least the ground probe pin is configured to pierce an oxide layer over a ferrule of a filtered feed-through assembly under test to securely form the ground connection.

2. The test system of claim 1 wherein the conductor probe pin and the ground probe pin of the plurality of pins directly contact one of the conductive lines and the ferrule, respectively, of the filtered feed-through assembly during measurement of the one or more electrical parameters of the filtered feed-through assembly under test.

3. The test system of claim 1 wherein the measurement meter is controllable to provide an alternating current signal at one or more frequencies to the filtered feed-through assembly under test during measurement of the one or more electrical parameters of the filtered feed-through assembly under test.

4. The test system of claim 1 wherein the processor of the control module is operable to execute instructions stored in memory to:

determine insertion loss data at a high frequency;
determine a set of ESR data at a low frequency;
determine an ESR limit at a low frequency;

determine an ESR value for a manufactured filtered feed-through assembly; and determine quality of the manufactured filtered feed-through assembly based upon the ESR limit.

5. The test system of claim 1 wherein the test system further comprises a plurality of conductor probe pins arranged to contact a plurality of conductive lines of a filtered feed-through assembly, and further wherein the test system comprises a switch matrix electrically coupled to the plurality of conductor probe pins of the test fixture via a plurality of selectable channels and also electrically coupled to the measurement device, wherein the control module is coupled to the switch matrix to control selection of one of the plurality of selectable channels to selectively couple the measurement meter to a selected conductor probe pin.

6. The test system of claim 1 wherein the processor is operable to execute instructions to apply regression analysis to correlate ESR data and insertion loss data.

7. The test system of claim 1 wherein the processor is operable to execute instructions to correlate ESR data and insertion loss data for a set of filtered feed-through assemblies and to determine an ESR limit based on the correlation and on a selected desired insertion loss limit.

8. The test system of claim 1 wherein the processor is operable to execute instructions to:
 determine insertion loss data for a set of filtered feed-through assemblies based upon a first high frequency signal;
 determine insertion loss data for the set of filtered feed-through assemblies based upon a second high frequency signal;
 determine ESR data for the set of filtered feed-through assemblies based upon a low frequency signal;
 apply regression analysis to the ESR data and insertion loss data;
 create a prediction interval for insertion loss defined by an upper limit and a lower limit;
 acquire the selected desired insertion loss limit representative of the desired minimal quality that is sought for a manufactured filtered feed-through assembly; and
 determine the ESR limit based on the selected desired insertion loss limit and the upper limit defined for the prediction interval.

9. A method comprising:
 correlating, with a processor executing instructions, ESR data and insertion loss data for one or more filtered feed-through assemblies and determining an ESR limit at a low frequency based on the correlation and a selected desired insertion loss limit;
 determining an ESR value for a manufactured filtered feed-through assembly; and
 determining quality of the manufactured filtered feed-through assembly based on a comparison of the ESR value to the ESR limit.

10. The method of claim 5 further comprising:
 forming a secure ground connection between a ferrule of the manufactured filtered feed-through assembly and a pin of a test fixture used to determine the ESR value.

11. The method of claim 9 further comprising:
 rejecting the manufactured feed-through assembly if the ESR value exceeds the ESR limit.

12. The method of claim 9, wherein correlating, with the processor executing instructions, ESR data and insertion loss data for one or more filtered feed-through assemblies comprises applying regression analysis to ESR data and insertion loss data.

13. The method of claim 9, wherein correlating, with the processor executing instructions, ESR data and insertion loss data for one or more filtered feed-through assemblies comprises correlating ESR data and insertion loss data for a set of filtered feed-through assemblies.

14. The method of claim 9, wherein correlating, with the processor executing instructions, ESR data and insertion loss data for one or more filtered feed-through assemblies comprises:
 determining insertion loss data for a set of filtered feed-through assemblies based upon a first high frequency signal;
 determining insertion loss data for the set of filtered feed-through assemblies based upon a second high frequency signal;
 determining ESR data for the set of filtered feed-through assemblies based upon a low frequency signal;
 applying regression analysis to the ESR data and insertion loss data;
 creating a prediction interval for insertion loss defined by an upper limit and a lower limit;
 acquiring the selected desired insertion loss limit representative of the desired minimal quality that is sought for a manufactured filtered feed-through assembly; and
 determining the ESR limit based on the selected desired insertion loss limit and the upper limit defined for the prediction interval.

15. A method comprising:
 correlating, with a processor executing instructions, ESR data and insertion loss data for a set of filtered feed-through assemblies and determining an ESR limit at a low frequency based on the correlation and a selected desired insertion loss limit;
 determining an ESR value for a manufactured filtered feed-through assembly;
 determining quality of the manufactured filtered feed-through assembly based on a comparison of the ESR value to upon the ESR limit;
 forming a secure ground connection between a ferrule of the manufactured filtered feed-through assembly and a pin of a test fixture used to determine the ESR value; and
 rejecting the manufactured feed-through assembly if the ESR value exceeds the ESR limit.

16. The method of claim 15 wherein correlating, with the processor executing instructions, ESR data and insertion loss data for the set of filtered feed-through assemblies comprises:
 determining insertion loss data for a set of filtered feed-through assemblies based upon a first high frequency signal;
 determining insertion loss data for the set of filtered feed-through assemblies based upon a second high frequency signal;
 determining ESR data for the set of filtered feed-through assemblies based upon a low frequency signal;
 applying regression analysis to the ESR data and insertion loss data;
 creating a prediction interval for insertion loss defined by an upper limit and a lower limit;
 acquiring the selected desired insertion loss limit representative of the desired minimal quality that is sought for a manufactured filtered feed-through assembly; and
 determining the ESR limit based on the selected desired insertion loss limit and the upper limit defined for the prediction interval.

* * * * *